United States Patent [19]

Reiner et al.

[11] 4,157,440

[45] Jun. 5, 1979

[54] THERAPEUTICALLY ACTIVE D-GLUCOSAMINE SALTS

[75] Inventors: Alberto Reiner, Como; Giacinto Rossi, Banchette, both of Italy

[73] Assignee: Marxer S.p.A., Twin, Italy

[21] Appl. No.: 560,236

[22] Filed: Mar. 20, 1975

[30] Foreign Application Priority Data

Apr. 2, 1974 [IT] Italy ............................. 49967 A/74

[51] Int. Cl.$^2$ ........................................... C07H 19/20
[52] U.S. Cl. ..................................... 536/27; 424/180; 536/18; 536/28
[58] Field of Search ................ 260/211.5 R; 424/180; 536/27

[56] References Cited

U.S. PATENT DOCUMENTS

| | | | |
|---|---|---|---|
| 2,710,860 | 6/1955 | Ruskin | 260/211.5 R |
| 3,856,776 | 12/1974 | Gehovic et al. | 260/211.5 R |

*Primary Examiner*—Johnnie R. Brown
*Attorney, Agent, or Firm*—Cushman, Darby & Cushman

[57] ABSTRACT

For the treatment of cardiac hypertrophy, d-glucosamine salts of the 3',5'-adenosine monophosphoric cyclic acid (AMP-c) and of the dibutyl ester thereof are disclosed, these salts having a reduced acute toxicity and an improved activity on the mitochondria of hypertrophic heart with respect to the cyclic AMP acid alone or its dibutyl ester. The compounds in question are useful for the treatment of cardiac hypertrophy and alteration of the energetic muscular metabolism.

5 Claims, No Drawings

THERAPEUTICALLY ACTIVE D-GLUCOSAMINE SALTS

This invention relates to d-glucosamine salts, as obtained by quaternization of the amine nitrogen of glucosamine with organic compounds which contain in their molecule a phosphorus group in the form of a cyclic diester of a nucleoside.

More specifically, the present invention has as its subject-matter d-glucosamine salts having the following structural formula:

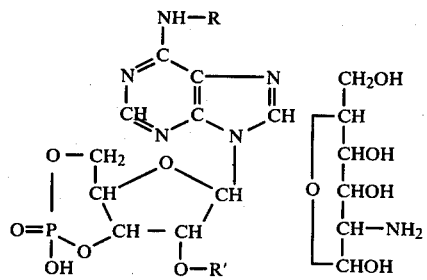

wherein R and $R_1$ are a hydrogen atom or the group

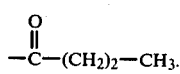

Stated otherwise, the subject-matter is d-glucosamine salts of the cyclic 3', 5'-adenosinemonophosphoric acid (indicated in the following, as is usual, as AMP-c) and of the dibutyl ester of 3', 5'-cyclic AMP.

These salts which, during progress of the pharmacological tests, have proven to possess, over the corresponding cyclic AMP acid or its dibutyl ester, a lesser acute toxicity and to unfold a greater activity on the mitochondria of hypertrophic hearts at the instant of their maximum functional engagement.

The preparation of the novel compounds according to the present invention takes place by direct reaction between stoichiometric amounts of d-glucosamine base in aqueous solution and cyclic 3', 5'-adenosime monophosphoric acid, the reaction being carried out at a temperature not over 6°–7° C. and under a nitrogen atmosphere. Salification occurs immediately and the completion of the reaction is potentiometrically controlled.

The chemical isolation of the novel salts according to the present invention takes place by freeze-drying, due to the extreme sensitivity of the products which are highly sensitive in solution to a number of agents, such as oxygen, temperature and others, which, with the lapse of time, are conducive to degradation products.

On the contrary, the products which have been isolated by means of organic solvents, are deliquescent, it is difficult to obtain them in the crystalline conditions and they are much less stable in time.

By way of example only and without limitation, a few examples of preparation of the compounds according to the present invention will be indicated.

EXAMPLE 1 d-glucosamine cyclic 3', 5'-adenosine triphosphate

A 5.26% aqueous solution of glucosamine base is prepared and is maintained in a pure nitrogen stream, the temperature of the solution being not higher than 6°–7° C. Slowly, and bubbling a stream of pure nitrogen therethrough, there is added to the solution in increments the stoichiometrically calculated amount of cyclic 3', 5'-AMP acid. Salification takes place immediately and is potentiometrically calculated, the operation being completed at a final pH of about 6.2.

This solution is concentrated in a vacuo in a rotating evaporator at a temperature equal to or less than 40° C. and the evaporation is brought about nearly to dryness.

The residue left in the flask is taken up with a minimum amount of methanol, the final salt being then precipitated by addition of 10 volumes of anhydrous acetone, with stirring and at a temperature equal to or not higher than 10° C. The product is quickly collected on a Buchner funnel, thoroughly washed with acetone and dried to constant weight in a vacuo. The product which is obtained is in the form of deliquescent white crystals.

The product, analyzed gives:

| For $C_{16}H_{25}N_6O_{11}P$ | | |
|---|---|---|
| | Calculated | Found |
| C % = | 37.8 | 36.5 |
| N % = | 16.531 | 16.3 |
| P % = | 6.1 | 5.9 |
| H % = | 4.957 | 4.8 |
| Mol. wt. = | 508.39 | |

EXAMPLE 2 d-glucosamine-N-6, 2'-dibutyryl-adenosine-3', 5'-monophosphate

The reaction is carried out through two discrete stages, consisting in setting free the N-6, 2'-dibutyryl-adenosine-3', 5'-monophosphoric acid from its sodium salt and its subsequent salification with glucosamine base.

The setting free of the N-6, 2'-d butyryl-adenosine-3', 5'-monophosphoric acid is effected by using a cationic resin chromatographic column, known with the trade name of Amberlite IR 120, activated in the acidic form.

There are weighed 9 grams of the sodium salt of the dibutyryl-adenosine-3', 5'-monophosphoric acid, which are dissolved in 100 mls distilled water, saturated with pure nitrogen, and having a temperature of 5° C. The chromatographic column is filled with 25 mls of the above mentioned cationic resin, activated with 4%-HCl and washed with water to neutrality.

The solution of the sodium salt is then passed through the columns, whose eluate is immediately cooled to 3° C. Then, under a stream of pure nitrogen and at the above indicated temperature, 3.05 grams of glucosamine base in the form of a 5.26% solution are slowly dripped. The final pH of the solution is 5.3.

Freeze-drying process is carried out on the thusly obtained solution, such as disclosed in Example 1 above, and a compact, microcrystalline and very stable but strongly hydroscopic product is obtained.

The product analyzes:

| For $C_{24}H_{37}N_6O_{13}P$ | | |
|---|---|---|
| | Calculated | Found |
| C % = | 44.44 | 44.11 |
| H % = | 5.743 | 5.6 |
| N % = | 12.95 | 12.3 |
| P % = | 4.77 | 4.62 |

The compounds according to the present invention have been pharmacologically investigated with a view to evaluating the acute toxicity and the general tolerability.

As far as acute toxicity is concerned, this has been determined with the Miller and Tainter method (Proc. Soc. Expl. Biol. Med., 57, 261, 1944) on Swiss mice and the following results have been obtained:

glucosamine salt of the 3', 5'-cyclic AMP acid:
$DL_{50}=1230+71.73$ mg/kg intraperitoneally
3', 5'-Cyclic AMP-dibutyryl-glucosamine:
$DL_{50}=980+78.76$ mg/kg intraperitoneally.

Such a toxicity is positively lower than that of the corresponding unsalified derivatives with glucosamine. More particularly, for cyclic 3', 5'-AMP acid, the acute toxicity in mice is:
$DL_{50}=520.5$ mg/kg subcutaneously, and
$DL_{50}=306.5$ mg/kg intraperitoneally.

Also the general tolerability tests have proven favourable.

As a matter of fact, dosages for 25, 50, 100 and 200 mg/kg of both the compounds of the present invention have been injected intravenously in the Wistar rat, recording in anaesthesis an arterial pressure in the carotid; ECG in second derivation and respiration during three hours after injection. On completion of these tests it has been ascertained that both the compounds do not produce, even at high dosages, toxic modifications of the above indicated parameters.

More detailed tests have been effected with the compounds of the present invention in order to evaluate the activity in the presence of heart hypertrophy, a condition which involves, as such, well known functional, structural and biochemical changes.

A more specific object of the tests was to check whether, by supplying the heart mitochondria in hypertrophic hearts (in the instant of their maximum functional engagement) with metabolites capable of stimulating the energetic systems, it is possible to protect these structures while preventing them from encountering hazardous energetic unbalance phenomena, which is the first step towards the clinical manifestation, that is the dynamic unbalance.

For the tests there have been used male rabbits weighing 2,000–2,500 grams in which myocardiac hypertrophy was obtained to the expenses of the left ventricle by surgically promoting an aortic valvular insufficiency by the introduction of a polyethylene catheter, according to the method by Quercio (Chir. e Patol. Sperim., 11, 185, 1963). In its turn, cardiac unbalance was induced by intramuscular injection of diphteric toxine.

Then there were determined in the animals:
(a) The heart weight/body weight ratio
(b) The oxidising phosphorilation
(c) The oxygen consumption, and
(d) The inorganic orthophosphate.

The test result makes conspicuous the fact that the d-glucosamine salt of cyclic AMP is capable of preventing, in the animals having hypertrophic heart and subjected to factors susceptible of inducing an unbalance, the unmatching of the oxidising phosphorilation, and thus allows a greater availability of energy for the myocardic cells, encouraging a more valid prolongation of the situation of dynamic balance.

It is furthermore apparent from the data as obtained that the activity of the glucosamine salt (dibutyryl) of cyclic AMP has an activity which is positively higher than that of the sodium salt of the cyclic AMP acid, which is incapable of preventing the unbalance as induced by the treatment with diphteric toxines. Also the results as obtained after hydric load indicate that with the cyclic AMP dibutyryl salt of d-glucosamine there are values of the P/O ratio which are definitely higher than those which are obtained with the dibutyl ester of the cyclic AMP acid.

It can thus be concluded that the d-glucosamine salt of the cyclic dibutiryl AMP exhibits a very satisfactory activity for the energetic balance of hypertrophic hearts as well as an improved activity over the corresponding unsalified compound. It seems thus that the salification with d-glucosamine is capable of potentiating the mechanism of action at the heart level by favoring the assumption and the utilization by the myocardial fibrous cellule.

What is claimed is:

1. d-glucosamine salts having the general formula:

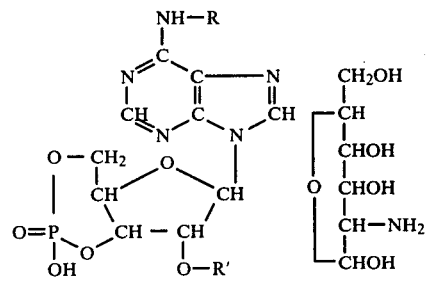

wherein R and $R_1$ are a hydrogen atom or

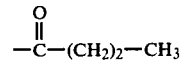

2. d-glucosamine salt according to claim 1, which is cyclic 3', 5'-adenosine phosphate of d-glucosamine.

3. d-glucosamine salt according to claim 1, which is N-6, 2'-dibutyryl-adenosine-3', 5'-monophosphate of the d-glucosamine.

4. A method for the preparation of the d-glucosamine salts having the formula as claimed in claim 1, wherein stoichiometrical amounts of d-glucosamine base in aqueous solution and 3', 5'-adenosine monophosphoric acid are brought to reaction under a nitrogen atmosphere and at a temperature not over 6°-7° C. and the product of the reaction is isolated in a freeze-dried form.

5. A method according to claim 4, wherein the sodium salt of the N-6, 2'-dibutyryl-adenosine-3', 5'-monophosphoric acid is treated in a chromatographic column with a strong cationic resin activated in acidic form to set free the corresponding acid, which, in an aqueous solution maintained at a temperature not over 7° C. and saturated with nitrogen, is brought stoichiometrically to react under nitrogen with d-glucosamine in aqueous solution and the reaction product is isolated by freeze-drying.

* * * * *